(12) United States Patent
Goffena et al.

(10) Patent No.: US 7,279,208 B1
(45) Date of Patent: *Oct. 9, 2007

(54) THIN-WALL POLYTETRAFLUOROETHYLENE TUBE

(75) Inventors: Donald G. M. Goffena, Camp Verde, AZ (US); David J. Myers, Camp Verde, AZ (US)

(73) Assignee: Gore Enterprise Holdings, Inc, Newark, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/510,937

(22) Filed: Feb. 22, 2000

Related U.S. Application Data

(63) Continuation of application No. 08/247,960, filed on May 24, 1994, now Pat. No. 6,027,779, which is a continuation-in-part of application No. 08/204,708, filed on Mar. 2, 1994, now Pat. No. 6,025,044, which is a continuation-in-part of application No. 08/108,963, filed on Aug. 18, 1993, now Pat. No. 6,159,565.

(51) Int. Cl.
   B29D 22/00 (2006.01)
   B29D 23/00 (2006.01)
   B32B 1/08 (2006.01)
(52) U.S. Cl. .................. 428/36.91; 428/421; 604/509; 604/96.01; 623/900
(58) Field of Classification Search ............ 428/36.91, 428/35.8, 36.1, 411.1, 421; 623/900; 604/96, 604/508, 509
See application file for complete search history.

(56) References Cited

U.S. PATENT DOCUMENTS

| 3,657,744 A | 4/1972 | Ersek |
| 3,868,956 A | 3/1975 | Alfidi et al. |
| 3,953,566 A * | 4/1976 | Gore ........................ 264/288 |
| 4,055,696 A | 10/1977 | Kamada et al. |
| 4,106,509 A * | 8/1978 | McWhorter ................ 604/129 |
| 4,130,904 A | 12/1978 | Whalen |
| 4,140,126 A | 2/1979 | Chodury |
| 4,187,390 A * | 2/1980 | Gore ..................... 174/102 R |
| 4,190,909 A | 3/1980 | Ablaza |
| 4,250,138 A | 2/1981 | Okita |
| 4,313,231 A | 2/1982 | Koyamada |

(Continued)

FOREIGN PATENT DOCUMENTS

DE   3918736   12/1990

(Continued)

OTHER PUBLICATIONS

Balko A et al., Transfemoral Placement of Intraluminal Polyurethane Prosthesis for Abdominaol Aortic Aneurysm. J of Surg Research 1986; 40:305-309.

(Continued)

*Primary Examiner*—Michael Miggins
(74) *Attorney, Agent, or Firm*—Wayne D. House

(57) ABSTRACT

A thin-wall PTFE (polytetrafluoroethylene) tube in the form of a tube of porous expanded PTFE film wherein the porous PTFE film has a microstructure containing a multiplicity of fibrils. The thin-wall tube is used in a non-porous embodiment as the balloon portion of a balloon catheter. The thin-wall tube is not elastomeric; however, because of the thinness, strength and flexibility of the tube, it may be inserted into a body conduit in a collapsed state and then deployed from a catheter and inflated up to the maximum diameter of the thin-wall tube. The porous PTFE film is provided with a continuous layer of adhesive to provide the non-porous tube; the adhesive is preferably a thermoplastic and more preferably a thermoplastic fluoropolymer such as fluorinated ethylene propylene.

9 Claims, 11 Drawing Sheets

U.S. PATENT DOCUMENTS

| | | | |
|---|---|---|---|
| 4,347,204 A | 8/1982 | Takagi et al. | |
| 4,478,898 A | 10/1984 | Kato | |
| 4,512,338 A | 4/1985 | Balko et al. | |
| 4,553,545 A | 11/1985 | Maass et al. | |
| 4,562,596 A | 1/1986 | Kornberg | |
| 4,577,631 A | 3/1986 | Kreamer | |
| 4,613,544 A | 9/1986 | Burleigh | |
| 4,637,396 A | 1/1987 | Cook | |
| 4,650,466 A | 3/1987 | Luther | |
| 4,655,771 A | 4/1987 | Wallsten | |
| 4,681,110 A | 7/1987 | Wiktor | |
| 4,702,252 A | 10/1987 | Brooks et al. | |
| 4,706,670 A | 11/1987 | Andersen et al. | |
| 4,713,070 A | 12/1987 | Mano | |
| 4,718,907 A * | 1/1988 | Karwoski et al. | 623/23.71 |
| 4,764,560 A | 8/1988 | Mitchell | |
| 4,776,337 A | 10/1988 | Palmaz | |
| 4,787,899 A | 11/1988 | Lazarus | |
| 4,791,966 A | 12/1988 | Eilentropp | |
| 4,816,339 A | 3/1989 | Tu et al. | |
| 4,820,298 A | 4/1989 | Leveen et al. | |
| 4,832,688 A | 5/1989 | Sagae et al. | |
| 4,877,030 A | 10/1989 | Beck et al. | |
| 4,877,661 A * | 10/1989 | House et al. | 428/34.9 |
| 4,878,906 A | 11/1989 | Lindemann et al. | |
| 4,902,292 A * | 2/1990 | Joseph | 623/4 |
| 4,925,710 A * | 5/1990 | Buck et al. | 428/34.5 |
| 4,954,126 A | 9/1990 | Wallsten | |
| 4,955,899 A * | 9/1990 | Delia Corna et al. | 623/1 |
| 5,066,298 A | 11/1991 | Hess | |
| 5,078,726 A | 1/1992 | Kreamer | |
| 5,087,244 A | 2/1992 | Wolinsky et al. | |
| 5,107,852 A | 4/1992 | Davidson et al. | |
| 5,116,318 A | 5/1992 | Hillstead | |
| 5,122,154 A | 6/1992 | Rhodes | |
| 5,123,917 A | 6/1992 | Lee | |
| 5,151,105 A | 9/1992 | Kwan-Gett | |
| 5,152,782 A | 10/1992 | Kowligi et al. | |
| 5,156,620 A | 10/1992 | Pigott | |
| 5,201,706 A | 4/1993 | Noguchi et al. | |
| 5,211,658 A | 5/1993 | Clouse | |
| 5,213,576 A | 5/1993 | Abiuso et al. | |
| 5,225,131 A | 7/1993 | Tamaru | |
| 5,236,447 A | 8/1993 | Kubo et al. | |
| 5,254,090 A | 10/1993 | Lombardi et al. | |
| 5,254,107 A * | 10/1993 | Soltesz | 604/282 |
| 5,256,143 A | 10/1993 | Miller et al. | |
| 5,286,254 A | 2/1994 | Shapland et al. | |
| 5,290,306 A | 3/1994 | Trotta et al. | |
| 5,366,472 A | 11/1994 | Hillstead | |
| 5,403,340 A | 4/1995 | Wang et al. | |
| 5,425,710 A | 6/1995 | Khair et al. | |
| 5,456,661 A | 10/1995 | Narciso, Jr. | |
| 5,458,568 A | 10/1995 | Racchini et al. | |
| 5,478,320 A | 12/1995 | Trotta | |
| 5,490,839 A | 2/1996 | Wang et al. | |
| 5,498,238 A | 3/1996 | Shapland et al. | |
| 5,499,980 A | 3/1996 | Euteneuer | |
| 5,500,180 A | 3/1996 | Anderson et al. | |
| 5,752,934 A * | 5/1998 | Campbell et al. | 604/96.01 |
| 5,972,441 A * | 10/1999 | Campbell et al. | 428/34.1 |
| 6,025,044 A * | 2/2000 | Campbell et al. | 428/36.91 |
| 6,027,779 A * | 2/2000 | Campbell et al. | 428/36.91 |
| 6,027,811 A * | 2/2000 | Campbell et al. | 428/411.1 |

FOREIGN PATENT DOCUMENTS

| | | | |
|---|---|---|---|
| EP | 5367109 | | 6/1978 |
| EP | 0 372088 | | 6/1990 |
| EP | 0 461791 | | 12/1991 |
| EP | 0 464755 | | 1/1992 |
| EP | 0 466518 | | 1/1992 |
| EP | 0 480667 | | 4/1992 |
| EP | 0 508473 | | 10/1992 |
| EP | 0 518704 | | 12/1992 |
| EP | 0 528039 | | 2/1993 |
| EP | 0 539237 | | 4/1993 |
| JP | 5536492 | | 5/1976 |
| JP | 60172306 | | 9/1985 |
| WO | WO 90140646 A | * | 11/1990 |
| WO | 9112779 | | 9/1991 |
| WO | 9402185 | | 2/1994 |

OTHER PUBLICATIONS

Chuter TAM et al., Transfemoral Endovascular Aortic Graft Placement. J of Vas Surg 1993; 18(2):185-197.

Cragg AH, Drake MD, Percutaneous Femoropopliteal Graft Placement. Radiology 1993; 187(3):643-648.

Dillon ME, Silicone and Poly(tetrafluoroethylene) Interpenetrating Polymer Networks. 1994 American Chemical Society.

George PJM et al., Covered expandable metal stent for recurrent tracheal obstruction. Lancet 1990; 335:582-584.

Kato M et al., Development of a chronic endothelialized transcatheter implantable intra-aortic graft. ASAIO Jour 1993; M518-521.

Lawrence DD et al., Percutaneous Endovascular Graft: Experimental Evaluation. Radiology 1987; 163(2):357-360.

Mirich D et al., Percutaneously Placed Endovascular Grafts for Aortic Aneurysms: Feasibility Study. Radiology 1989; 170(3):1033-1037.

Parodi JC et al., Transfemoral Intraluminal Graft Implantation for Abdominal Aortic Aneurysms. Annals Vas Surg 1991; 5(6):491-499.

Preminger TJ et al., Transluminal vascular stenting using a GORE-TEX covered stent: An experimental study. Presented at Congress of Pediatric Cardiology and Cardiac Surgery Jun. 21-25, 1993.

Sayers RD et al., Endovascular stenting of abdominal aortic aneurysms. Eur J Vasc Surg 1993; 7:225-227.

Schenck RR and Derman GH. An Intraluminal Silastic Stent for Small Vessel Repair. Orth Clin N.A. 1977; 8(2):265-271.

Yoshida H et al., Transcatheter Placement of an Intraluminal Prosthesis for the Thoracic Aorta, A New Approach to Aortic Dissections. ASAIO Transactions 1991; 37:M272-273.

Yoshioka T et al, Self-Expanding Endovascular Graft: An Experimental Study in Dogs. AJR 1988; 151:673-676.

Notice of Opposition to European Patent EP 714,487 to W. L. Gore & Assoc. Inc. by Meadox Medicals, Inc.(including Facts and Arguments) Jan. 21, 1999.

* cited by examiner

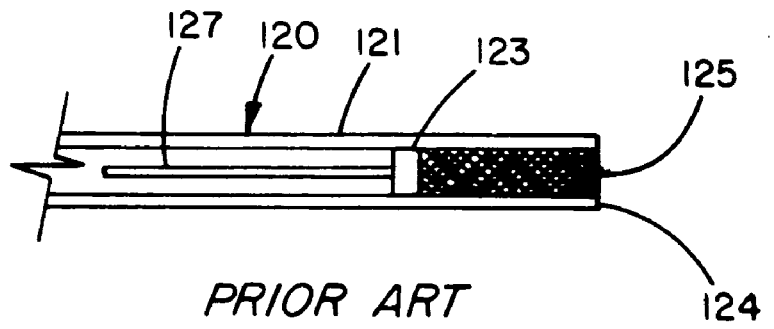
PRIOR ART
FIG. 12A
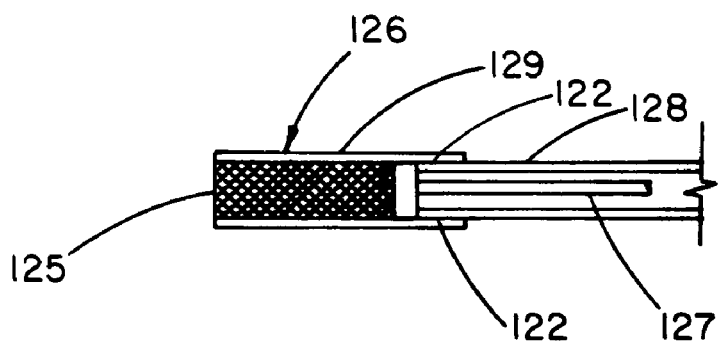
FIG. 12B
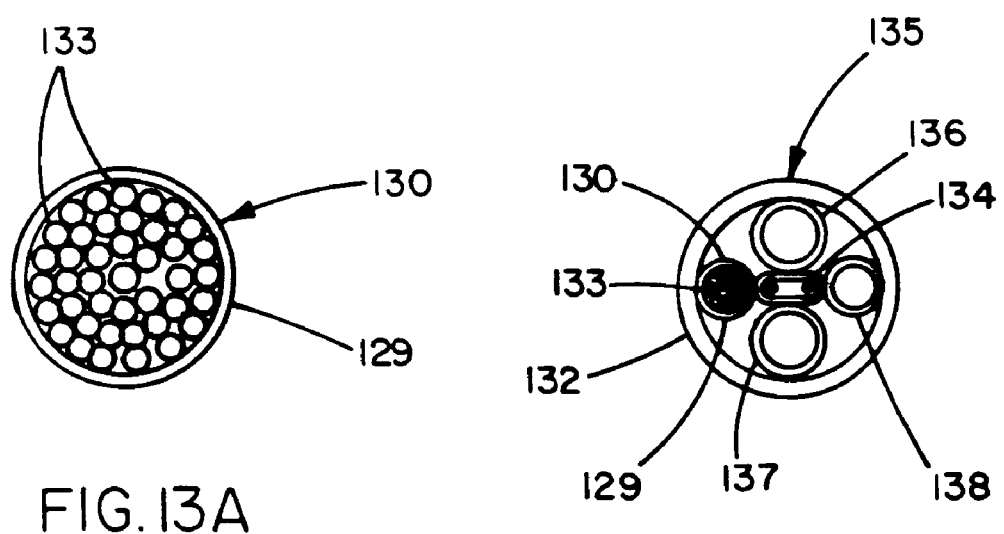
FIG. 13A
FIG. 13B

THIN-WALL POLYTETRAFLUOROETHYLENE TUBE

CROSS-REFERENCE TO RELATED APPLICATIONS

The present application is a continuation of application Ser. No. 08/247,960 filed May 24, 1994, now U.S. Pat. No. 6,027,779, which is a continuation-in-part of application Ser. No. 08/204,708 filed Mar. 2, 1994, now U.S. Pat. No. 6,025,044, which is a continuation-in-part of application Ser. No. 08/108,963 filed Aug. 18, 1993, now U.S. Pat. No. 6,159,565.

FIELD OF THE INVENTION

This invention relates to the field of thin-wall polytetrafluoroethylene tubes.

BACKGROUND OF THE INVENTION

Thin-wall polytetrafluoroethylene (hereinafter PTFE) tubes are useful for a variety of applications where the thinness of the tube wall and the lubricity of the PTFE are advantageous. The chemically inert character of the PTFE is also advantageous, particularly when the biocompatibility of the tubing is a concern.

Conventional thin-wall PTFE tubes suffer from poor flexibility and have relatively poor mechanical strength characteristics, specifically tensile strength and hoop strength. Their resistance to creep when subjected to mechanical loads for extended periods of time is also poor. These conventional tubes also possess significant memory in that if subjected to, for example, a crease or kink, the tube will remember the crease or kink and will want to assume the same crease or kink subsequently if exposed to the slightest causative force.

U.S. Pat. No. 4,925,710 to Buck et al., describes a thin-wall sintered fluoropolymer tube having a wall thickness of less than about 0.051 mm. The tube is made by extruding a non-porous fluoropolymer tube over a fluoropolymer core containing a filler and subsequently removing the core. U.S. Pat. No. 4,791,966 to Eilentropp describes a PTFE tube made by helically wrapping a PTFE tape around a mandrel, sintering the wrapped tape to fuse the overlapping tape edges and finally removing the mandrel from the resulting tube. The tape is relatively thin, from 30 to 300 micrometers in thickness, and is of trapezoidal cross section wherein the tape edges are thinner than the center of the tape width, so that the overlapping edges of the helically-wrapped tape result in a tube of relatively uniform wall thickness. The tubes of Buck et al., and Eilentropp both suffer from the aforementioned disadvantages of poor mechanical strength characteristics, poor flexibility, and excessive memory.

U.S. Pat. Nos. 3,953,566; 3,962,153 and 4,197,390 to Gore describe making tubes and sheet films of porous expanded PTFE wherein the PTFE has a microstructure of nodes interconnected by fibrils. The tubes are made by extruding a paste of a mixture of PTFE fine powder and a liquid lubricant, removing the lubricant from the resulting tubular extrudate, expanding the extrudate by stretching at a suitable rate at a temperature less than the crystalline melt point of the PTFE, and preferably sintering the expanded PTFE tube while the tube is longitudinally restrained. These patents do not teach the construction of thin-wall tubes. Tubes made according to these patents are commercially available as vascular grafts (W.L. Gore & Associates, Inc., Flagstaff Ariz.) and are provided with an exterior helical wrapping of porous expanded PTFE film which increases the hoop strength of the tube.

SUMMARY OF THE INVENTION

The present invention is a thin-wall PTFE tube comprising a tube of porous expanded PTFE film wherein the porous expanded PTFE film has a microstructure containing a multiplicity of fibrils oriented substantially parallel to each other. The tube has a wall thickness of less than about 0.25 mm and preferably less than 0.1 mm wherein the tube comprises a first layer of porous expanded PTFE film and a second layer of porous expanded PTFE film wherein the fibrils of the first layer of porous expanded PTFE film are oriented substantially perpendicular to the fibrils of the second layer of porous expanded PTFE film. More preferably the fibrils of the first layer of porous expanded PTFE film are oriented substantially parallel to the longitudinal axis of the tube and the fibrils of the second layer of porous expanded PTFE film are oriented substantially circumferential to the tube.

The term expanded is used herein to refer to porous expanded PTFE. The terms expand, expanding and expandable are used herein to refer to diametrically-adjustable intraluminal stents.

The first layer is preferably the inner layer with the second layer serving as an outer layer. Alternatively, the relationship between the first and second layers may be reversed so that the second layer serves as the inner layer of the graft.

The inventive thin-wall PTFE tube has good hoop strength because of the circumferentially oriented layers of film. The tube is flexible and collapsible, thereby allowing it to be collapsed to a size much smaller than the full inside diameter. It has very little memory, so that such a tube that was previously collapsed and subsequently brought back to its full diameter does not retain the creases and wrinkles of its collapsed state. The thin-wall PTFE tube is therefore particularly useful as an intraluminal graft. Such a graft is capable of being implanted into a living body in the collapsed state and can therefore be inserted into a conveniently accessible, smaller diameter portion of a body conduit and then transferred to another, larger diameter portion of the body conduit where it is needed with the use of a catheter type of delivery system. One end of the intraluminal graft is then secured by suitable means such as the use of one or more metallic expandable stents. The use of the inventive intraluminal graft thus allows for the effective repair of living blood vessels without the trauma typically associated with conventional invasive vascular surgery.

The inventive tube may optionally incorporate separate longitudinally-oriented ribs intended to serve as additional strength members. These ribs may be in the form of, for example, stringers of PTFE or fluorinated ethylene propylene (hereinafter FEP) of small diameter such as about 0.025 mm to about 0.5 mm. The use of such longitudinally-oriented ribs can add significantly to the longitudinal strength of the tube without appreciably interfering with the ability of the tube to be collapsed in diameter for ease of insertion into a vascular system and then subsequently increased in diameter at a different location within the vascular system. These ribs may easily be incorporated into the tube during construction by temporarily attaching the ribs to the surface of a manufacturing mandrel prior to wrapping the mandrel with a layer of porous expanded PTFE film. The mandrel assembly can then be heated adequately to cause the ribs to adhere to the film, after which the mandrel can be removed. The ribs may be located on the luminal surface of the film, on the exterior surface of the film, or between two layers of the film.

Alternatively, either the first or second film layers may be replaced by alternative reinforcing components such as a braid or at least one reinforcing rib. If at least one reinforcing rib is used, the at least one rib should be oriented to be substantially perpendicular to the fibrils of the remaining film layer. In still another alternative, the braid or the at least one reinforcing rib may be used in conjunction with the aforementioned two-layer film construction. It is preferred that the braid or the at least one reinforcing rib be between the first and second film layers.

According to another embodiment, a metal reinforcing rib may be used. As described above, the reinforcing rib may be in the form of a braid which may be a braided wire. Preferably, such a braided wire reinforcement would be placed between the first and second layers of porous expanded PTFE film. Most preferably, the metal reinforcing rib is a stainless steel wire reinforcing rib wound helically about the tube and placed between the first and second layers of porous expanded PTFE film. Tubes made according to this construction may be made in a variety of diameters. For example, tubes having a diameter of about 2 mm or tubes of about 1 meter diameter may be made. Tubes of this type having a helically oriented reinforcing wire have good diametrical crush resistance and extremely good flexibility. Such tubes are anticipated to have applications including ducting of air or gas, especially of high temperature air or corrosive gases. They are also anticipated to have utility as flexible bellows for compression of air or gas, or as a flexible covering intended to exclude dirt from extensible mechanical devices. The wire reinforced tube is also expected to serve as an effective filter construction for gases or various liquids wherein the wire reinforcement provides an effective supporting framework for the porous expanded PTFE film. The film may be used as the filtration medium depending on the requirements of the application and porosity of the film, or alternatively an additional layer of an alternative filtering medium may be provided, preferably between the first and second layers of the porous expanded PTFE film. Because of the excellent flexibility of such a wire reinforced tube and because of the non-stick characteristics of the porous expanded PTFE film, such a filter tube may be flexed repeatedly to provide a cleaning function whereby flexing of the tube at desired intervals causes contaminants accumulated on the wall of the filter to break free from the filter wall to allow them to be collected and thereby allow subsequent continued use of the filter.

Optionally, metal wires to be used as reinforcing ribs may be provided with thermoplastic coatings or jackets prior to helical wrapping of the wire during construction of the thinwall tube. The use of such a jacket or coating is anticipated to improve adhesion between the wire and the porous expanded PTFE film.

For embodiments incorporating at least one reinforcing rib of any type, the wall thickness of the thin-wall tube is less than 0.25 mm and preferably less than 0.10 mm. This wall thickness is considered to be exclusive of the reinforcing rib and is therefore to be measured at locations on the thin-wall tube that do not include any part of a reinforcing rib in the wall thickness.

It is anticipated that the inventive tube will be useful for a variety of applications. In addition to intraluminal vascular grafts, air ducts, bellows and filtration applications, other applications may include various types of catheters such as collapsible catheters and everting catheters. The tubes may also be used to contain bundles of wires or wire-like components. For example because of the thin wall, lubricity and strength of the inventive tube, it may be useful as an encasing container for bundles of electrical conductors or fiber optic cables. Such a container is expected to be particularly useful for applications relating to temporary insertion of the contained bundle into a living body. The thinness, lubricity and strength of the inventive tube are also of value as a stent deployment device to temporarily cover the exterior surface of an implantable stent during insertion and deployment of the stent into a living body. The tube may also be useful as an introducer for other devices such as a gastroscope introducer whereby the tube is introduced into the esophagus of a patient after which a gastroscope or other endoscope is inserted through the tubing, thereby reducing the risk of injury to the patient with the gastroscope or endoscope. The inventive tubing is also anticipated to have other applications which may be medical or non-medical, these include applications as a vent material, filtration material or gas separation membrane material wherein the strength and/or thinness of the tube are advantageous. The tubing can also be made in either porous or non-porous embodiments.

BRIEF DESCRIPTION OF THE DRAWINGS

FIGS. 12A and 12B describe respectively longitudinal cross sectional views of prior art and inventive vascular stent deployment devices.

FIG. 13A describes a transverse cross sectional view of the thin-wall tube as an encasement for a bundle of fiber optic cables or electrical conductors.

FIG. 13B describes a transverse cross sectional view of the thin-wall tube as an encasement for a bundle of fiber optic cables or electrical conductors as typically used as a portion of an endoscope shaft.

DETAILED DESCRIPTION OF THE INVENTION

The porous expanded PTFE film from which the thin-wall tube of the present invention is constructed is made as taught by U.S. Pat. Nos. 3,953,566 and 4,187,390. These patents are herein incorporated by reference.

Figure 1:
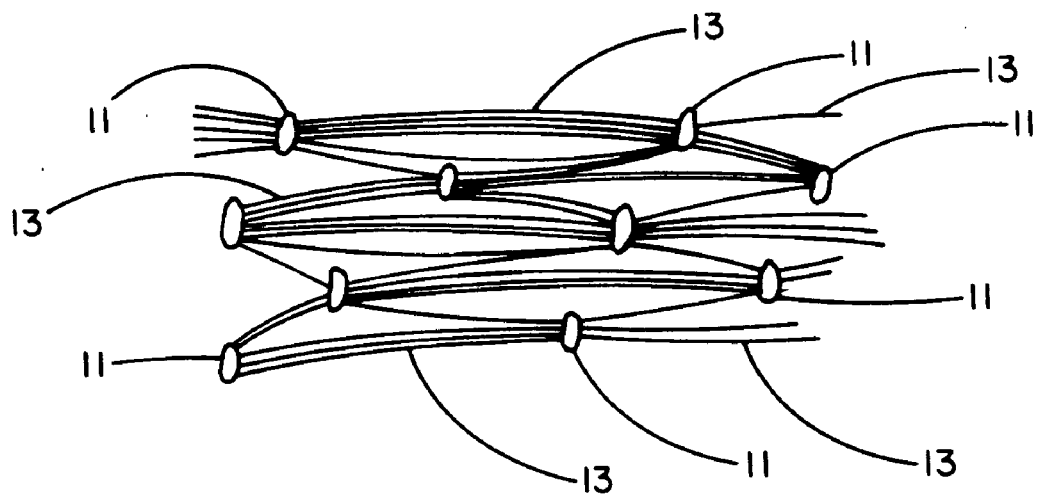
FIG. 1 describes an enlarged, schematic representation of the microstructure of the porous expanded PTFE film used to construct the thin-wall tube of the present invention.

As depicted by the enlarged, schematic representation of FIG. 1, these porous expanded PTFE films have a microstructure of nodes 11 interconnected by fibrils 13. These films are made by expansion by stretching in a single direction which is the direction in which the resulting fibrils are primarily oriented. As will be described, the thin-wall tube of the present invention is made of first and second layers of these films wherein the fibrils of the first layer are oriented parallel to the longitudinal axis of the thin-wall tube and the fibrils of the second layer are oriented substantially circumferential to the thin-wall tube.

The fibril lengths of the porous expanded PTFE films referred to herein were estimated mean values obtained by examining scanning electron photomicrographs of these films. The mean fibril lengths of the films used to construct the thin-wall tubes of the present invention are preferred to be within the range of about 5 to about 120 microns, although fibril lengths beyond this range may also be useful.

Figure 2:
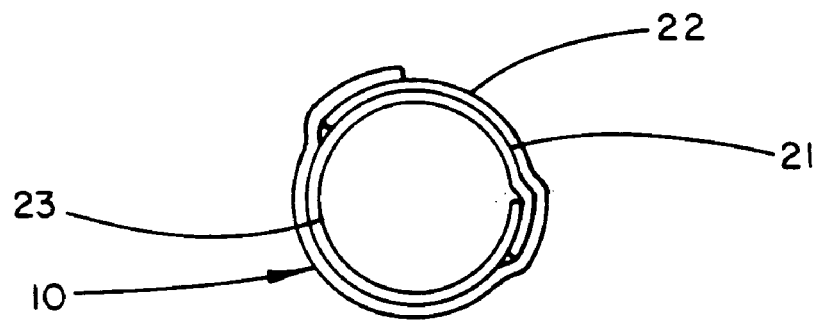
FIG. 2 describes a transverse cross section of the thin-wall tube having at least one substantially longitudinally-oriented first layer and at least one substantially circumferentially oriented second layer.
Figure 2A:
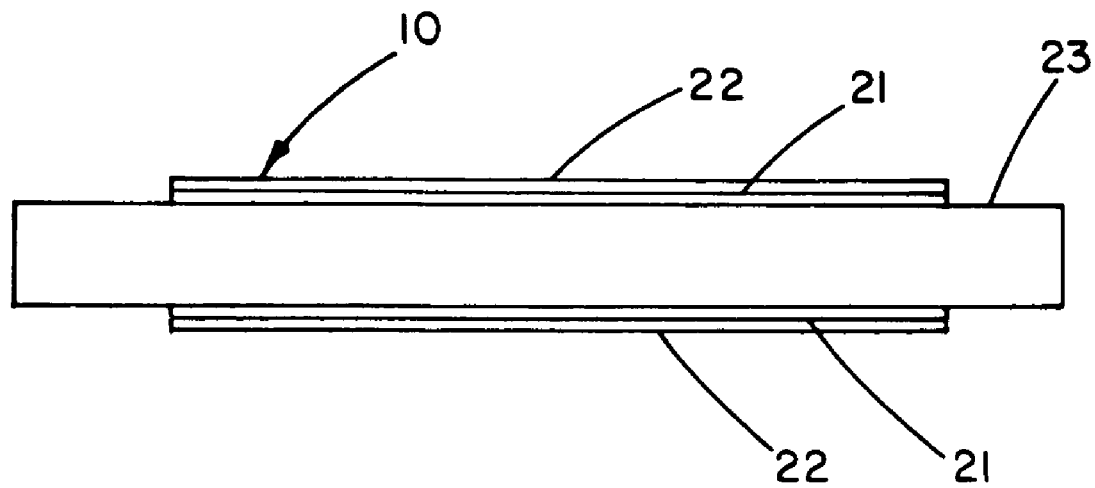
FIG. 2A describes a longitudinal cross section of the thin-wall tube of FIG. 2.

The thin-wall tube of the present invention is made by wrapping first and second layers of porous expanded PTFE film about a stainless steel mandrel of the same diameter as the desired diameter of the thin-wall tube. According to the embodiment described by the transverse cross section of FIG. 2 and the longitudinal cross section of FIG. 2A, the first layer 21 is first wrapped around the mandrel 23 with the fibrils of the film microstructure oriented longitudinally, that is, approximately parallel to the longitudinal axis of the mandrel and the thin-wall tube. The film should be of length at least equal to the desired length of the thin-wall tube, and of adequate width to allow the film to be fully wrapped around the mandrel surface thereby resulting in a tubular covering of longitudinally oriented film.

Figure 3:
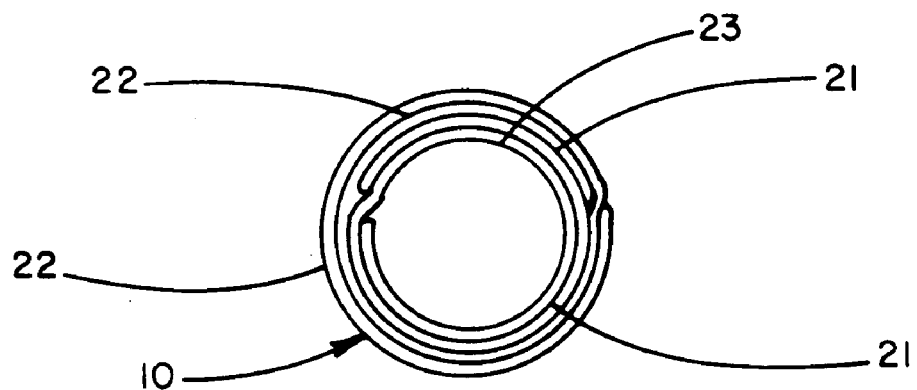
FIG. 3 describes a transverse cross section of the thin-wall tube having at least two substantially longitudinally-oriented first layers and at least two substantially circumferentially-oriented second layers.
Figure 3A:
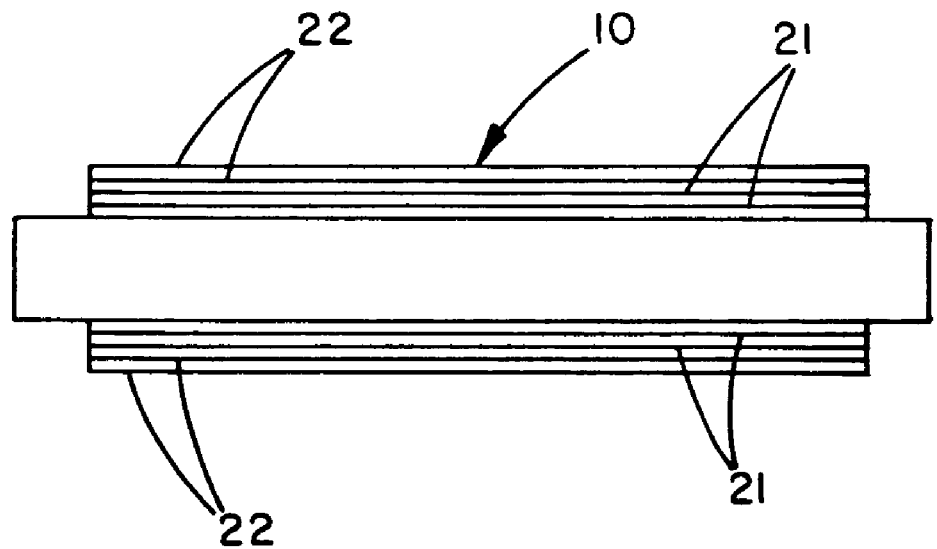
FIG. 3A describes a longitudinal cross section of the thin-wall tube of FIG. 3.

As described by the transverse cross section of FIG. 3 and the longitudinal cross section of FIG. 3A, the film of the first layer 21 may be of adequate width to allow wrapping at least twice around the surface of the mandrel 23 if desired, thereby resulting in at least two thicknesses of the first layer 21 of film.

The second layer 22 of film is then applied by wrapping porous expanded PTFE film circumferentially about the mandrel 23 and first layer 21 of film so that the fibrils of the microstructure of the second 22 layer are oriented substantially circumferentially around the mandrel 23 and first layer 21 of film. The second layer 22 of film should be of width at least equal to the desired length of the thin-wall tube 10. Again as shown by FIGS. 3 and 3A, the substantially circumferentially-oriented second layer 22 of film may be wrapped around the mandrel 11 and first layer 21 of film at least twice to provide for two or more thicknesses of film in the second layer.

Figure 4:
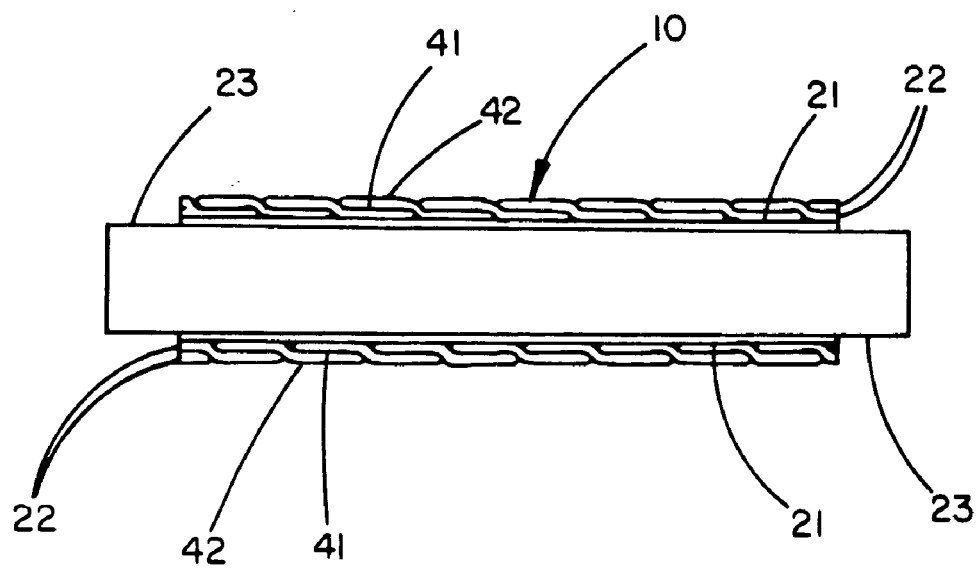
FIG. 4 describes an alternative embodiment of the thin-wall tube of FIG. 3 wherein the at least one substantially circumferentially-oriented second layer is a helically-wrapped outer layer.

Alternatively, a narrower film may be used for the second layer 22 if the film is wrapped helically about the mandrel 23 as described by the longitudinal cross section of FIG. 4. In this case the helically-wrapped film may be applied with a pitch that allows each wrap 42 of film to preferably overlap at least half of the width of the preceding wrap 41, thereby resulting in a second layer 22 of film that includes at least two thicknesses of substantially circumferentially-oriented film. Conversely, if it is desired to minimize the wall thickness of the thin-wall tube then a minimum amount of overlap may be used.

Figure 5:
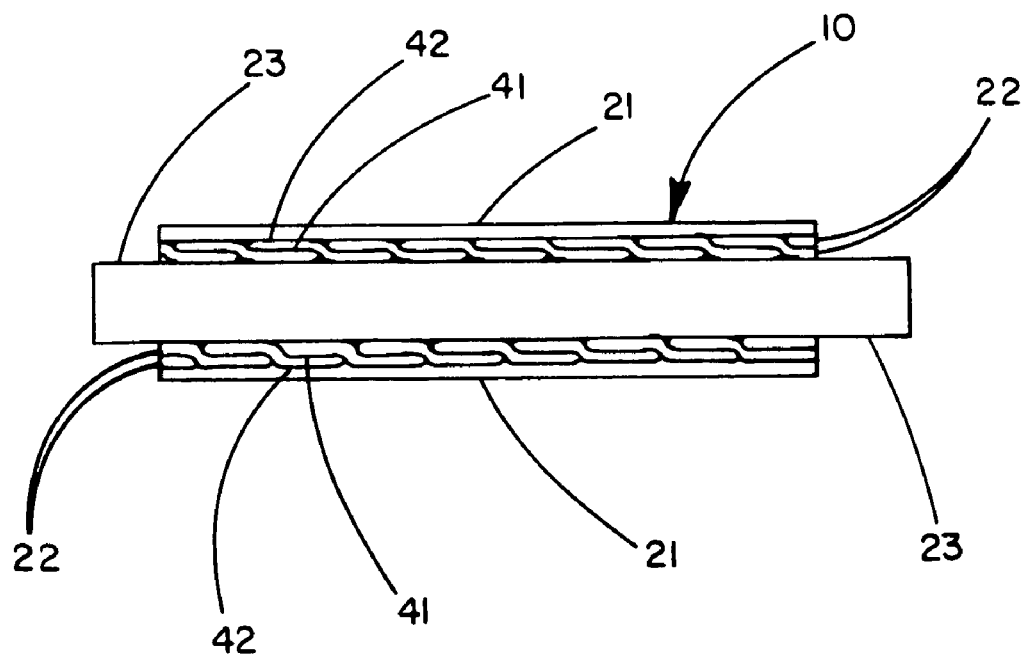
FIG. 5 describes an alternative embodiment of the thin-wall tube of FIG. 4 wherein the inner and outer relationships of the first and second layers are reversed.

If it is desired that the circumferentially-oriented second layer of film serve as the luminal surface of the thin-wall tube, then the application sequence of the first and second layers must be reversed as shown by the longitudinal cross section of FIG. 5.

The mandrel with the first and second layers of film is then heated adequately to cause adjacent layers of film to thermally bond to each other while limiting the applied heat so as not to cause significant damage to the microstructure of the films. The mandrel and films are then allowed to cool and the resulting thin-wall tube is removed from the mandrel. The ends of the thin-wall tube may then be trimmed off square with a sharp blade if desired.

The resulting thin-wall tube will be a porous construction resulting from the porous quality of the expanded PTFE film from which it is made. If a non-porous construction is desired, the thin-wall tube can be heated above the crystalline melt temperature of the PTFE to cause shrinkage of the porous expanded PTFE film until no porosity remains.

Non-porous or minimally porous constructions can also be made by the use of more layers of porous PTFE film.

Alternatively, an adhesive may be used between the layers of PTFE film to adhere adjacent layers together. The PTFE film may be made with the adhesive on only one surface of the film. The adhesive coated films are oriented during wrapping of the mandrel so that the adhesive-coated side of the film contacts adjacent layers of film and does not contact the mandrel. The adhesive is preferably in the form of a discontinuous, porous coating in order to have a minimal effect on the porosity of the completed thin-wall tube. Alternatively, however, a continuous layer of adhesive may be used if a non-porous thin-wall tube is desired. The adhesive must be biocompatible for implantable applications; preferred adhesives are thermoplastics of lower melt point than the crystalline melt point of the PTFE film. Thermoplastic fluoropolymers such as FEP are most preferred. These types of adhesives are activated by placing the film-wrapped mandrel into an oven at a combination of time and temperature adequate to cause melting of the adhesive.

Figure 11A:
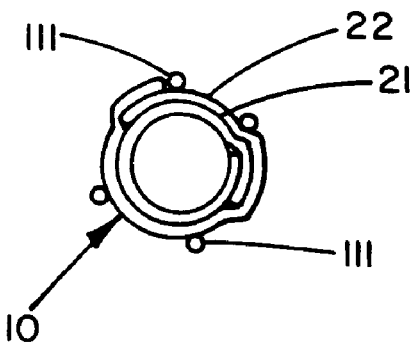
FIGS. 11A, 11B, 11C, 11D and 11E describe views of the thin-wall tube incorporating alternative reinforcing components.
Figure 11B:
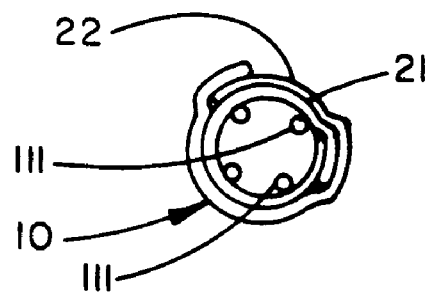
Figure 11C:
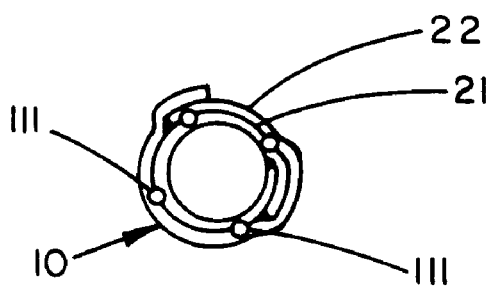

As previously described, the thin-wall tube may be provided with substantially longitudinally-oriented reinforcing ribs in the form of stringers of, for example, FEP or PTFE. The ribs are not limited to being oriented parallel to the longitudinal axis of the thin-wall tube, but may also be provided with a helical bias. FIG. 11A describes a cross sectional view of a thin-wall tube 10 with ribs 111 on the exterior surface. FIG. 11B describes a cross sectional view of a thin-wall tube 10 with ribs 111 on the luminal surface. FIG. 11C shows a cross sectional view having ribs 111 between two layers of film 21 and 22.

Figure 11D:
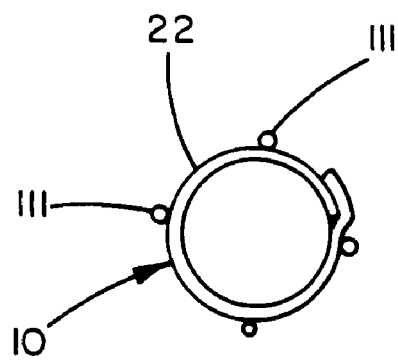
Figure 11E:
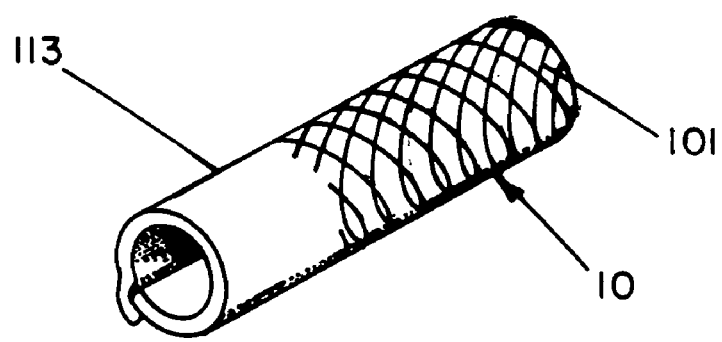

For the thin-wall tube of the present invention, either the first or the second layer of porous expanded PTFE film may be replaced by alternative reinforcing components such as a braid or at least one reinforcing rib. If at least one reinforcing rib is used, the orientation of the at least one rib should be substantially perpendicular to the orientation of the fibrils within the film layer. For example, as shown by FIG. 11D, the thin-wall tube 10 may comprise at least one layer of porous expanded PTFE film 22 having fibrils oriented substantially circumferential to the thin-wall tube and also have at least one substantially longitudinally-oriented reinforcing rib 111 on the exterior surface of film 22. Further, as shown by the perspective view of FIG. 11E, the thin-wall tube may also be provided with an alternative reinforcing component in the form of a braid 101 on the exterior surface of the film 113 wherein the film fibrils may be oriented either substantially longitudinal or substantially circumferential. Conversely, the braid 101 or substantially longitudinally-oriented reinforcing ribs 111 may be provided on the luminal surface of the thin-wall tube 10.

Likewise, at least one layer of porous expanded PTFE film having fibrils oriented to be substantially parallel to the longitudinal axis of the thin-wall tube may also be provided with a reinforcing braid or at least one reinforcing rib. For this embodiment, the orientation of the at least one reinforcing rib should be circumferential or helical. The at least one reinforcing rib may therefore be a single helically oriented reinforcing rib. These reinforcing components may be provided on either the exterior or luminal surfaces.

For embodiments wherein one of the layers of porous PTFE film is replaced by an alternative reinforcing component in the form of a braid or at least one reinforcing rib, the thickness of the film layer does not include the thickness of the alternative reinforcing component.

The figures beginning with FIG. 12B describe various applications of the thin-wall PTFE tube of the present invention. The thinness, flexibility, lubricity and mechanical strength of the thin-wall tube are of particular utility for these applications.

FIGS. 12A and 12B describe respectively longitudinal cross sectional views of prior art and inventive vascular stent deployment devices. In the prior art device 120, a catheter tube 121 encloses a vascular stent 125 which is intended to be deployed out of the end 124 of the catheter tube 121 by a pusher 123 affixed to a wire 127 to which is applied a pushing force from the proximal end of the catheter tube 121. This type of vascular stent deployment device is most useful for stents of the self-expanding type such as Nitinol wire stents. The inventive stent deployment device 126 uses a thin-wall PTFE tube 129 of the present invention to enclose the vascular stent 125 and also to attach the stent 125 to a catheter tube 121 until deployment in the same fashion as the prior art device 120. The thin-wall PTFE tube 129 is attached to catheter tube 121 at common surface 122. The thin-wall PTFE tube 129 allows the overall diameter of the stent delivery device to be reduced as the catheter tube 128 has an outside diameter equal to that of the stent 125, whereas the prior art device requires the catheter tube 121 to have an inside diameter larger than the outside diameter of the stent 125. A comparison of FIGS. 12A and 12B illustrates this.

In FIG. 13A the inventive thin-wall PTFE tube 129 is shown as the enclosure 130 that holds together a bundle of fiber optic strands 133 or electrical conductors 133. The thin wall, lubricity and mechanical integrity of the thin-wall tube result in an improved enclosure. One such application for this enclosure is within the bore of an endoscope as described by FIG. 13B. A typical endoscope 135 contains within its tubular housing 139 various components including manipulation wire channel 134, working channel 136, illumination channel 137, and enclosure 130 housing the bundle of fiber optic strands 133 or electrical conductors 133.

Figure 14A:
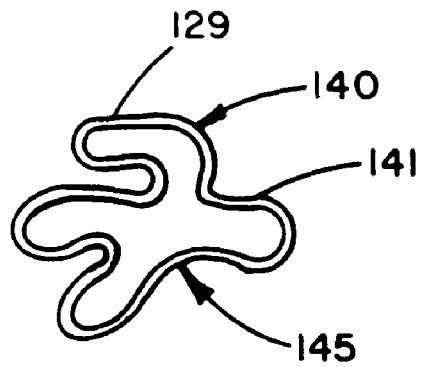
FIG. 14A describes a transverse cross sectional view of the thin-wall tube in a collapsed condition as used for a collapsible catheter or gastroscope prior to introducing a fluid or gastroscope into the thinwall tube.
Figure 14B:
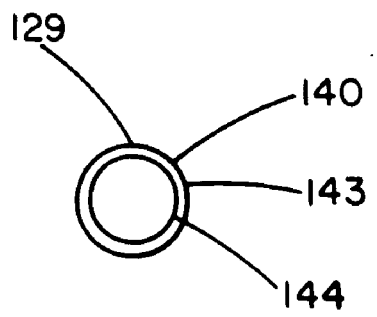
FIG. 14B describes a transverse cross sectional view of the thin-wall tube in use as a collapsible catheter after the introduction of fluid into the catheter.

FIG. 14A depicts a transverse cross section of the thin-wall tube 129 in a collapsed state as it would appear in use as a collapsible catheter 140 or a gastroscope introducer 145. As a collapsible catheter 140, the thin-wall tube 129 preferably in a nonporous configuration, can be introduced into a body cavity and left in its collapsed state as shown by FIG. 14A in order to minimize the amount of space occupied by the catheter. When needed, the collapsible catheter may be used to introduce, for example, a fluid 144 to a desired site within a living body as shown by the transverse cross section of FIG. 14B. Pressure applied to fluid 144 to ensure flow will partially or entirely bring the collapsible catheter 140 to its full volume as shown by the circular cross sectional shape of FIG. 14B. When fluid delivery is complete, the catheter 140 will revert to the collapsed state illustrated by FIG. 14A until needed again.

Figure 14C:
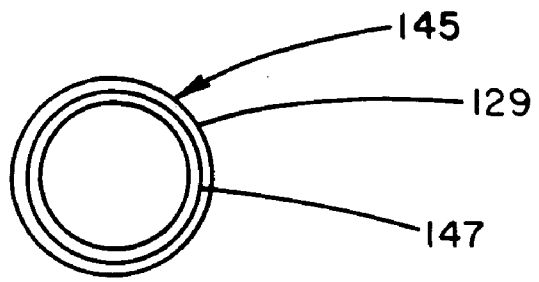
FIG. 14C describes a transverse cross sectional view of the thin-wall tube in use as a gastroscope introducer after the introduction of a gastroscope into the thin-wall tube.

The thin-wall tube is also useful as a gastroscope introducer 145 wherein a thin-wall PTFE tube 129 of the present invention is introduced in a collapsed state as suggested by the cross section of FIG. 14A into the esophagus of a patient. As shown by the transverse cross section of FIG. 14C, a gastroscope 147 may then be introduced into the patient through the thin-wall tube 129. The strength and lubricity of the thin-wall tube facilitate the introduction of the gastroscope into the esophagus with reduced risk of injury to the esophagus.

Figure 15:
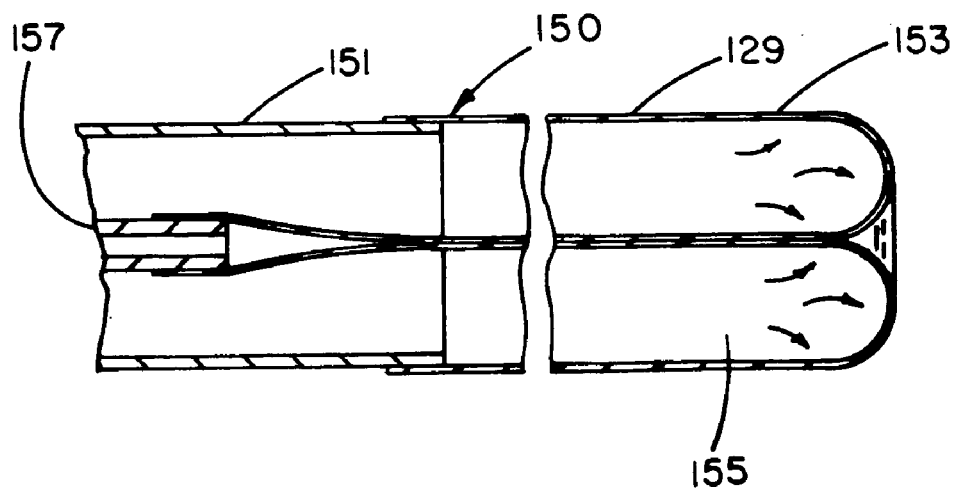
FIG. 15 describes a longitudinal cross sectional view of the thin-wall tube as the tubular everting portion of an everting catheter.

FIG. 15 describes a longitudinal cross section of an everting catheter 150 wherein the thin-wall PTFE tube 129, preferably in a nonporous configuration, constitutes the everting portion 153 of the catheter 150. Everting catheters 150 are typically used to deliver another fluid delivery catheter 157 or alternatively another device into a delicate, small diameter vessel that is vulnerable to damage by more conventional catheters. When fluid pressure is applied to volume 155, the everting portion 153 extends as it everts while gently pulling fluid catheter 157 into a desired site. The thinness, lubricity and mechanical strength of the thin-wall PTFE tube 129 are expected to be particularly useful when the tube 129 is used as the everting portion 153 of everting catheter 150.

Figure 16A:
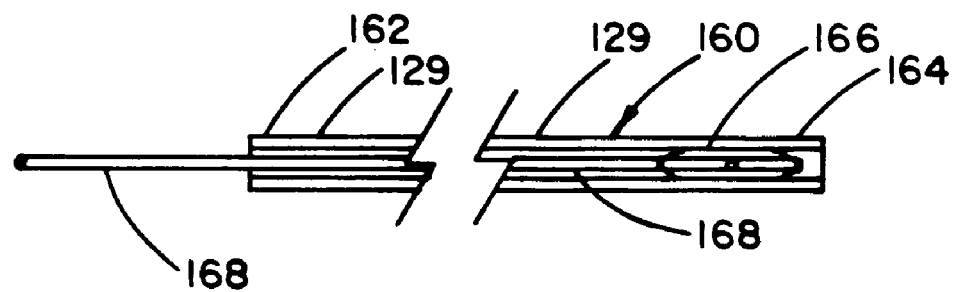
FIGS. 16A and 16B describe a longitudinal cross section of the thin-wall tube in use as a sleeve component of a balloon catheter for use during insertion of the balloon catheter into a vascular conduit.
Figure 16B:
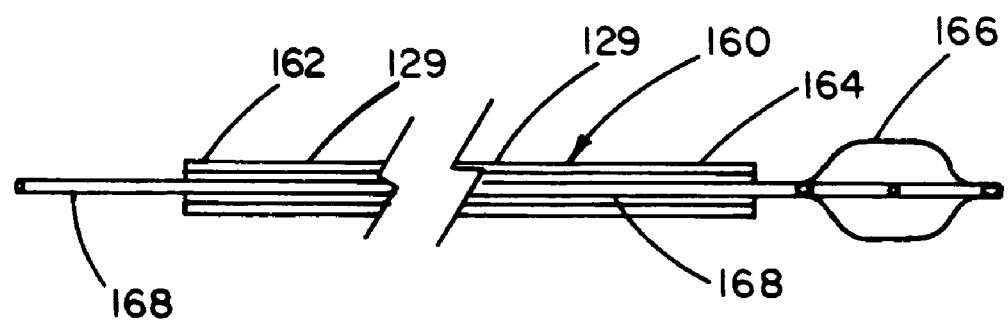

FIGS. 16A and 16B show the thin-wall PTFE tube 129 in use with a balloon catheter 160 wherein the thin-wall tube 129 retains the balloon 166 in a collapsed state during insertion of the balloon catheter 160 into a vascular conduit. When located as desired, the balloon 166 is deployed from the distal end 164 of the thin-wall tube 129 by applying tension to the proximal end 162 of the thin-wall tube 129 with respect to axial compression simultaneously applied to the balloon inflation tube 168. Balloon 166 may then be inflated as shown in FIG. 16B.

Figure 17:
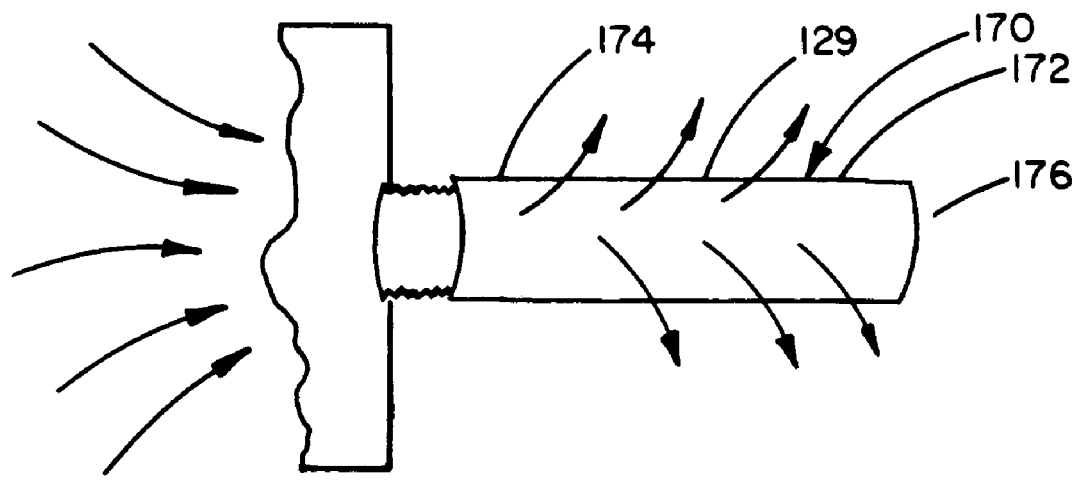
FIG. 17 describes the inventive tube in use as a filter bag.

As shown by FIG. 17, the inventive tube 129 may also be used as a filter bag 170. The porosity of the film from which such a tube can be made can be controlled as necessary for filtration applications by making the film according to the methods of U.S. Pat. Nos. 3,953,566 and 4,187,390. A filter bag made from the inventive tube can be quite strong due to the laminated construction of two layers laid up at right angles. The strength of the tube allows the tube to be used as a filter bag with minimal frame support or with no additional support. The end 172 of the tube 129 opposite the air inlet end 174 may be sealed in any suitable manner, such as by sewing, with an adhesive, by fitting a circular plug, or by a combination of these methods.

Figure 18A:
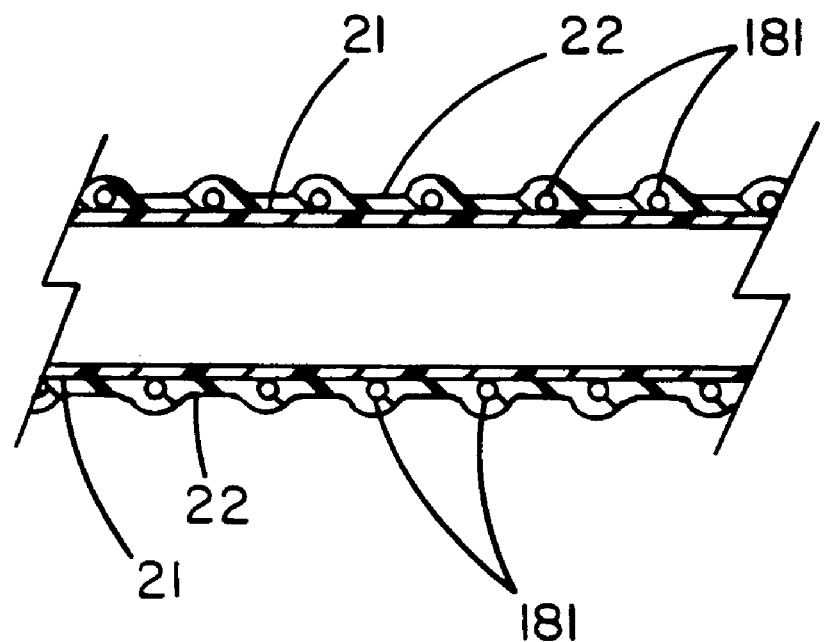
FIG. 18A describes a longitudinal cross sectional view of the thin-wall tube incorporating a helically-oriented wire as a metal reinforcing rib.
Figure 18B:
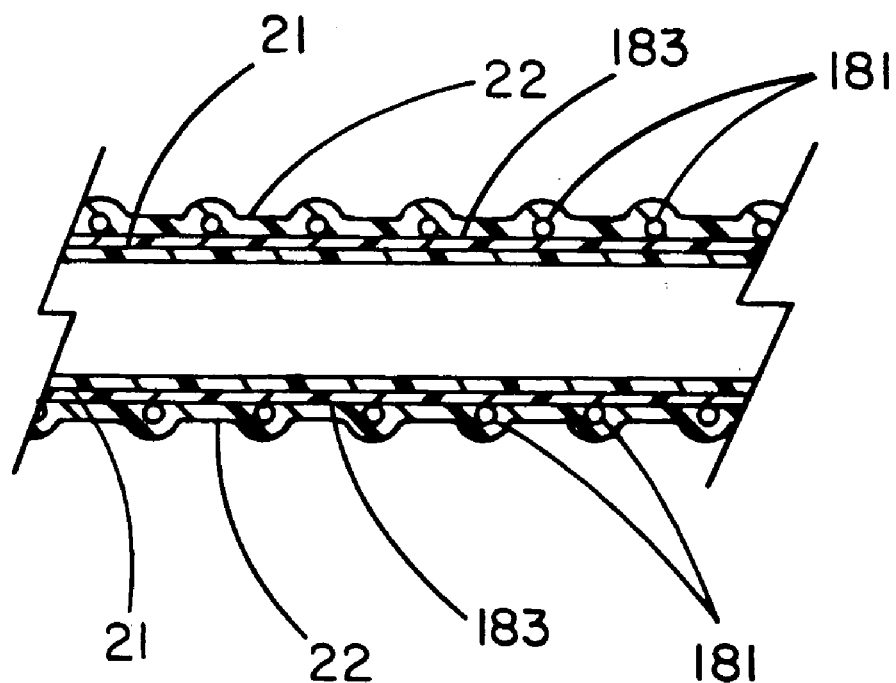
FIG. 18B describes a longitudinal cross sectional view of the thin-wall tube of FIG. 18A incorporating an additional layer of filtration material.

FIGS. 18A and 18B describe longitudinal cross sectional views of the thin-wall tube incorporating a helically-oriented metal wire 181 as a reinforcing rib between the first layer 21 and second layer 23 of porous expanded PTFE film. For filtration applications, as shown by FIG. 18B an additional layer of filtration material 183 may be incorporated as a filtration medium to trap contaminants above a desired size. While the filtration material 183 is preferably located between first layer 21 and second layer 23, the filtration material may alternatively be located on either the inner or outer surfaces of the thin-wall tube.

Figure 19:
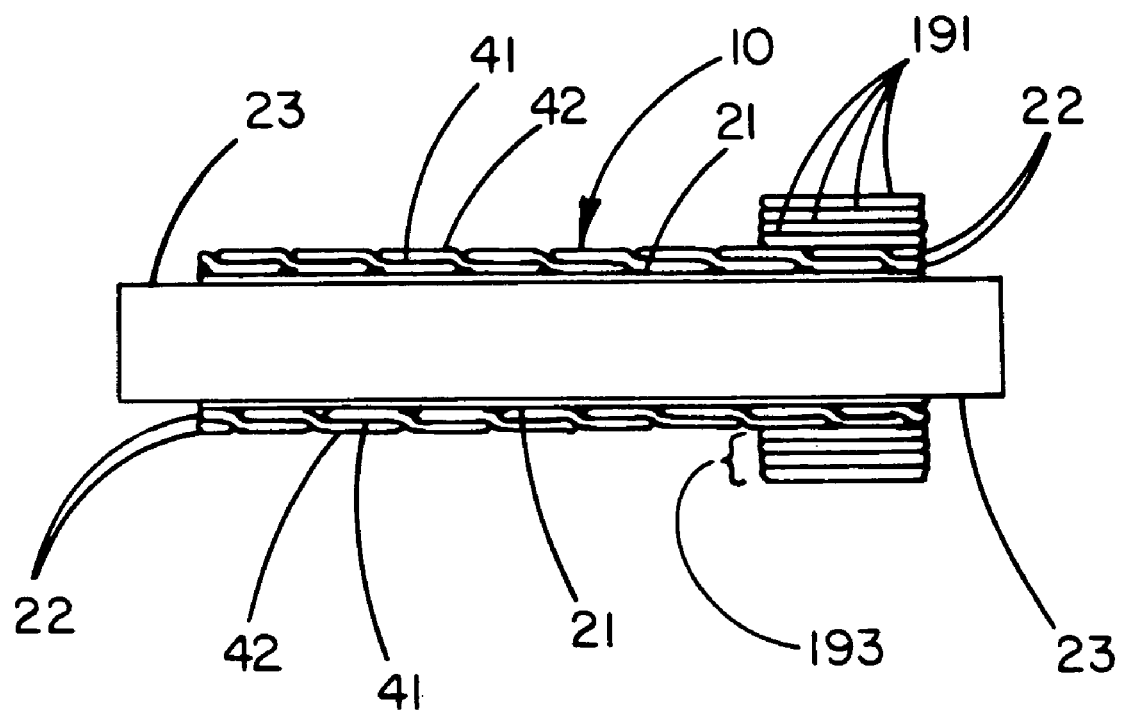
FIG. 19 describes a longitudinal cross section of the thin-wall tube incorporating a circumferential reinforcing rib at one end of the tube.

FIG. 19 describes a longitudinal cross section of the thin-wall tube incorporating a circumferential reinforcing rib 193 at one end of the tube. The circumferential reinforcing rib preferably comprises multiple layers 191 of the same helically-wrapped porous expanded PTFE film that comprises the second layer 22. Such a reinforcing rib is easily made during the process of providing the helical wrap by simply allowing the wrap to accumulate to the desired thickness at the end of the wrapping process. The circumferential reinforcing rib may be desirable for any application that may benefit from having an end of the tube stiffened. For example, if the tube is used for filtration applications it may be more easily fitted over or more easily clamped and sealed to a supply pipe if it has been provided with a circumferential reinforcing rib.

Figure 20:
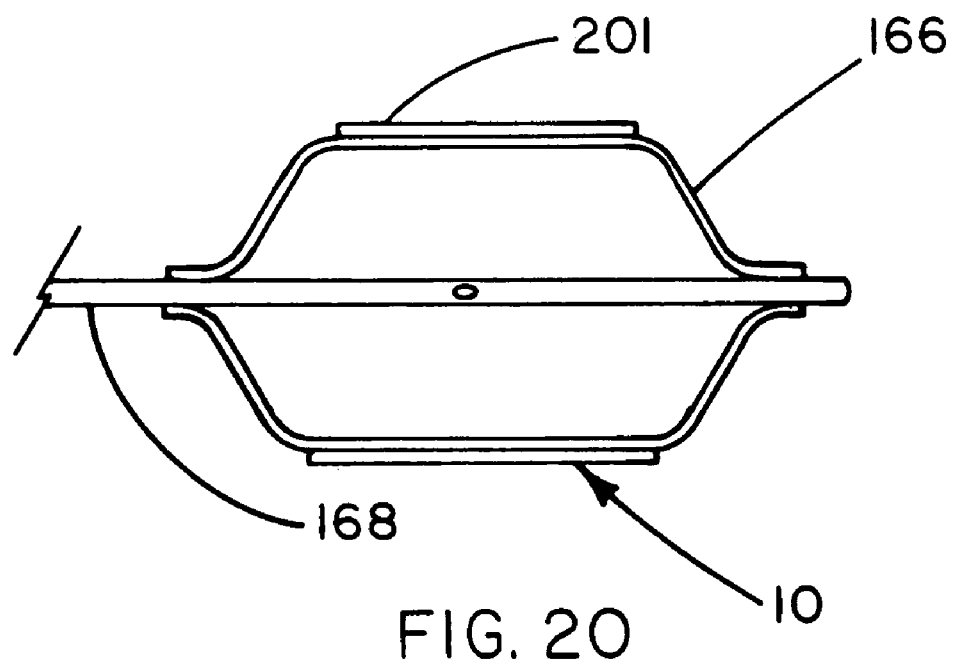
FIG. 20 describes a longitudinal cross section showing the thinwall tube in use as a cover for the balloon portion of a balloon catheter intended to limit the inflated diameter of the balloon portion thereby preventing overinflation and rupture of the balloon portion.

The thin-wall tube may also be used in a non-porous embodiment as the balloon portion of a balloon catheter. The thin-wall tube is not elastomeric in the fashion of a conventional balloon portion of a balloon catheter; however, because of the thinness, strength and flexibility of the inventive tube, it may be inserted in a collapsed state as suggested by the cross section of FIG. 14A and then deployed from a catheter and inflated up to the maximum diameter of the thin-wall tube in the manner of a conventional balloon as suggested by FIG. 16B. Likewise, as shown by FIG. 20, the thin-wall tube 10 in either a porous or non-porous embodiment may be used as a balloon cover 201 around the exterior surface of a conventional balloon 166 to limit the maximum diameter to which the balloon 166 may be inflated and thereby preventing overinflation and potential rupture of balloon 166.

EXAMPLE 1

A thin-wall tube was constructed by wrapping porous expanded PTFE film about an 8 mm diameter cylindrical stainless steel mandrel and then heating the film-wrapped mandrel. A 60 cm length of porous expanded PTFE film was wrapped around the surface of the mandrel with the fibrils of the film oriented parallel to the longitudinal axis of the mandrel. The film used was of about 0.03 mm thickness, 40 mm width, 40 micron fibril length, and about 0.3 g/cc density. The density of non-porous PTFE is about 2.2 g/cc; consequently the chosen film was about 86% porous. All film thickness measurements for each example were made with a Mitutoyo model no. 2804-10 snap gauge having a part no. 7300 frame, by placing a film sample between the measuring pads of the gauge and gently easing the pads into contact with the film sample until the pads were in full contact with the film sample under the full force of the spring-driven snap gauge. Film density values were based on the bulk volume of a film sample using the snap gauge thickness measurement.

Figure 6:
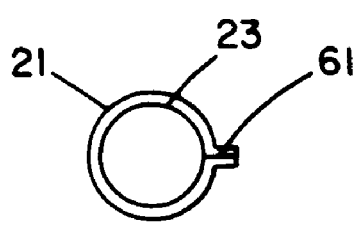
FIG. 6 describes a method of forming a seam with the edges of the first layer of film.

A flanged seam was formed as shown by the transverse cross section of FIG. 6; the contacting surfaces 61 of the flanged seam of the first layer 21 were heated with a hand-held iron by pressing the flanged seam between the iron and a sheet of polyimide film. The temperature of the heated surface of the iron was about 380° C. Excess film outside of the sealed portion of the seam was trimmed away with a scalpel blade and discarded.

Figure 6A:
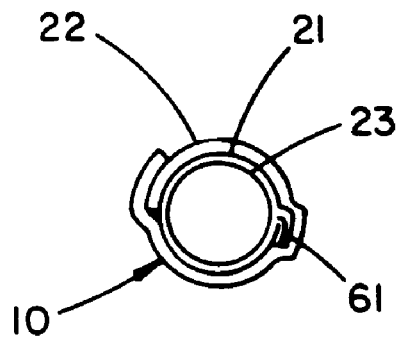
FIG. 6A describes fitting a second layer of film to the embodiment of FIG. 6.

As described by the transverse cross section of FIG. 6A, a second layer 22 of film was then applied about the surface of the first, longitudinally-oriented layer 21 by helically wrapping the second layer 22 over the surface of the first layer 21. The film used was of about 0.03 mm thickness, 12.5 mm width, 50 micron fibril length, and about 0.3 g/cc density. Each wrap 42 of the helically-oriented wrapping overlapped the adjacent wrap 41 by half of the width of the adjacent wrap 41 as depicted by FIG. 4. The mandrel 23 was first helically wrapped in one direction, followed by a second helical wrapping applied in the opposite direction which resulted in a total thickness of four layers of helically applied film. The mandrel 23 having the longitudinally-oriented first layer 21 and helically-oriented second layers 22 of film was then placed into an oven set at 385° C. for twenty minutes after which it was removed from the oven and allowed to cool. The heating process caused the helically oriented second layer 22 of film to shrink in a direction parallel to the direction of the fibrils, that is, circumferential to the surface of mandrel 23. The amount of heat used was adequate to cause adjacent contacting surfaces of the film to thermally bond together.

After the mandrel 23 was removed from the finished thin-wall tube 10, the wall thickness of the thin-wall tube was measured by transversely cutting off a short length of the thin-wall tube, longitudinally slitting the tube to form a sheet and then measuring the thickness of the sheet with the precision snap gauge. The thickness was determined to be about 0.07 mm. The mechanical integrity of a 10 cm long sample of this tube was challenged by inserting a latex balloon of 8 mm unpressurized diameter into the lumen of the sample and pressurizing the balloon with air at a pressure of 3.5 kg/cm$^2$ for 3 minutes. Inflation to this pressure required about five seconds of time which was not included in the 3 minute test time. This test caused no visible damage to the thin-wall tube.

EXAMPLE 2

Figure 7:
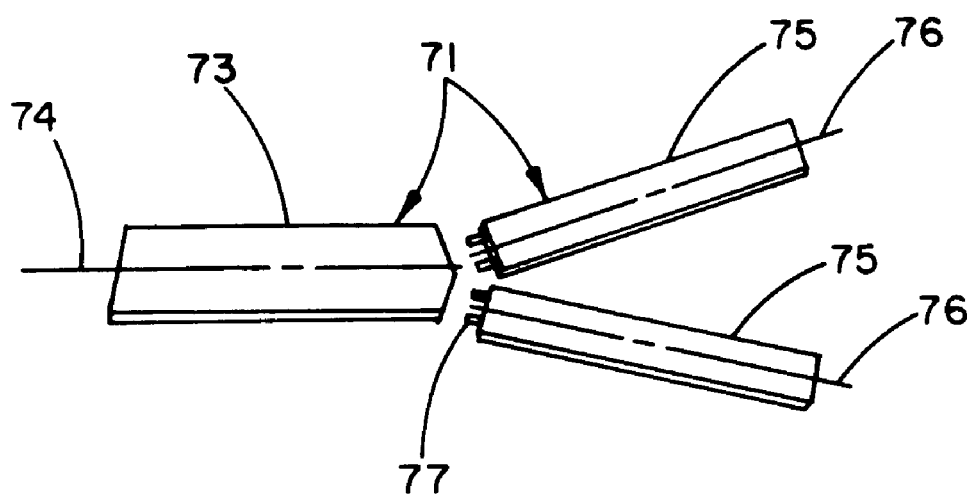
FIG. 7 describes a mandrel useful for constructing a bifurcated thin-wall tube of the present invention.

A bifurcated thin-wall tube was made by first constructing a flat mandrel 71 from 1.5 mm thick stainless steel as shown by FIG. 7; the mandrel 71 was cut into a Y-configuration wherein the trunk 73 was about 18 mm wide and legs 75 of the mandrel 71 were about 10 mm wide; the trunk 73 and legs 75 were each of about 80 mm length; the centerline 76 of each leg 75 diverged from the centerline 74 of the trunk 73 by an angle of about 15 degrees. The legs 75 were made as separate pieces and were retained to the trunk 73 in a removable fashion by the use of pins 77. All edges of the mandrel 71 were radiused.

The completed mandrel was placed between 2 layers of the same film used previously for the longitudinally-oriented film of Example 1. The fibrils of the layers of film were oriented parallel to the longitudinal axis of the trunk of the mandrel. The edges of the film were sealed together and trimmed around the perimeter of the flat mandrel in the same fashion as the edge of the longitudinally oriented film layer of Example 1.

Next, a helical wrapping of 12.5 mm wide film was applied by hand around the trunk and individual legs of the mandrel. The film used for the helical wrapping was a porous expanded PTFE film with an additional layer or coating of FEP on one surface. The FEP layer allows for subsequent thermal bonding of the film at a lower temperature than required for the PTFE-only film so that shrinkage of the PTFE film during the heating process may be substantially avoided.

The FEP-coated porous expanded PTFE film was made by a process which comprises the steps of:
a) contacting a porous PTFE substrate, usually in the form of a membrane or film, with another layer which is preferably a film of FEP or alternatively of another thermoplastic polymer;
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching and the thickness of the adhesive prior to stretching.

The FEP-coated porous expanded PTFE film used to make this example had a thickness of about 0.03 mm, a density of about 0.3 g/cc, a fibril length of about 80 microns, and a width of about 12.5 mm. This film used FEP as the continuous layer of thermoplastic fluoropolymer adhesive. The FEP-coated side of the film was placed against the layer of longitudinally-oriented film so that the FEP-coated side of the film faced the mandrel surface and the porous expanded PTFE side of the film faced outward away from the mandrel surface.

After helical wrapping with the FEP-coated film, the film-covered mandrel was placed into an oven set at 360° C. for 4 minutes. After removal from the oven, the assembly was allowed to cool. The sealed edges of film at the ends of the trunk and legs of the mandrel were trimmed away with a scalpel blade allowing the mandrel to be removed from the completed, bifurcated thin-wall tube by separating the legs from the trunk of the mandrel. The portion of the thin-wall tube between the legs was re-sealed with the hand iron to ensure the integrity of that region. The thickness of the wall of completed bifurcated thin-wall tube was measured to be about 0.10 mm.

EXAMPLE 3

A thin-wall tube of the type described in Example 1 was constructed of a discontinuous FEP-coated film. Examination of the FEP-coated side of the film by scanning electron microscopy revealed FEP on only small portions of the nodes and fibrils at the surface of the film. It was estimated that less than 10% of the available node and fibril surface area exposed at the surface of the film was covered by FEP. The presence of the FEP adhesive thus had little or no adverse effect on the porosity of the porous PTFE layer of the film. This FEP-coated film was about 0.01 mm thick, of about 50 micron fibril length and had a density of about 0.3 g/cc.

Figure 8:
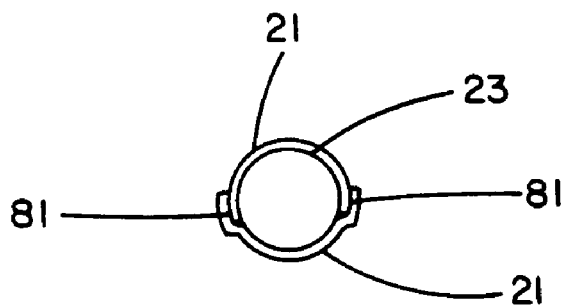
FIG. 8 describes an alternative method to that described by FIG. 6 for forming seams with the edges of the first layer of film.

The first layer 21 of film was applied by wrapping a 6 mm diameter cylindrical stainless steel mandrel 23 with two 12.5 mm wide strips of the FEP-coated porous expanded PTFE film as shown by the transverse cross section of FIG. 8. The edges 81 of the two layers of longitudinally-oriented film overlapped by about 3 mm. The PTFE side of the film was against the surface of the mandrel with the FEP coating facing away from the mandrel surface. The fibrils of the PTFE layer were oriented parallel to the longitudinal axis of the mandrel. A helically-wrapped second layer was then applied using a 12.5 mm wide strip of the same type of discontinuous FEP-coated film with the FEP-coated side of the film facing inward in contact with the FEP-coated surface of the longitudinally oriented layer. Each wrap of the helically-wrapped film overlapped three-quarters of the width of the previous wrap. The wrapping was applied in only one direction with the result that the helical wrapping was four layers thick due to the overlapping of the film during helical wrapping. The film-wrapped mandrel was then placed into an oven set at 325° C. for 20 minutes after which it was removed and allowed to cool. The mandrel was then removed from the completed thin-wall tube. The wall thickness of this example was determined to be about 0.06 mm.

EXAMPLE 4

Figure 9:
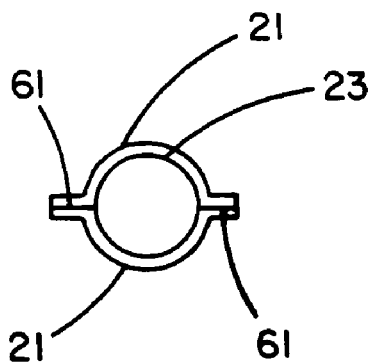
FIG. 9 describes an alternative method to that described by FIG. 8 for forming seams with the edges of the first layer of film.

A thin-wall tube was constructed by wrapping porous expanded PTFE film about a 6 mm diameter cylindrical stainless steel mandrel and then heating the film-wrapped mandrel. As described by the transverse cross section of FIG. 9, a first layer 21 of film was formed by wrapping two 120 cm lengths of porous expanded PTFE film around the surface of the mandrel 23 with the fibrils of the film oriented parallel to the longitudinal axis of the mandrel, forming flanged seams 61. The film used was of about 0.01 mm thickness, 12.5 mm width, 50 micron fibril length, and about 0.3 g/cc density. This film did not have an FEP coating. The flanged seams were heat-sealed and trimmed in a fashion similar to that described in Example 1.

Figure 9A:
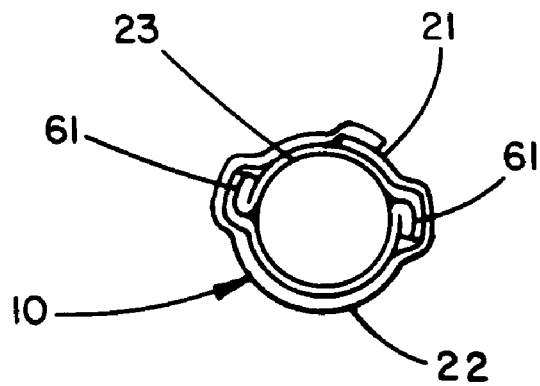
FIG. 9A describes fitting a second layer of film to the embodiment of FIG. 9.

As shown by the transverse cross section of FIG. 9A, a second layer 22 of the same film was then applied about the surface of the first, longitudinally-oriented layer 21 by helically wrapping the second layer 22 over the surface of the first layer 21. Each wrap of the helical wrapping overlapped the adjacent wrap by about 1 mm. The mandrel was helically wrapped in one direction only. This resulted in a thickness of one layer of helically applied film as measured at any transverse cross section, except for the 1 mm wide overlapped areas which were two layers in thickness. The mandrel having the longitudinally and helically-oriented coverings of film was then placed into an oven set at 383° C. for 15 minutes after which it was removed from the oven and allowed to cool. The resulting thin-wall tube was then removed from the mandrel. The heating process caused the helically-oriented film to shrink in a direction parallel to the direction of the fibrils, that is, circumferential to the mandrel surface. The amount of heat used was adequate to cause adjacent contacting surfaces of the film to thermally bond together.

The wall thickness of the finished thin-wall tube was determined to be 0.033 mm where adjacent helical layers overlapped and 0.025 mm between overlapped edges. The mechanical integrity of a 12 cm long sample of this tube was challenged by inserting a latex balloon of about 6 mm outside diameter into the lumen of the sample and pressurizing the balloon with air at a pressure of 1 kg/cm$^2$ for 3 minutes. Inflation to this pressure required about three seconds of time which was not included in the 3 minute test time. This test caused no visible damage to the thin-wall tube.

EXAMPLE 5

Figure 10:
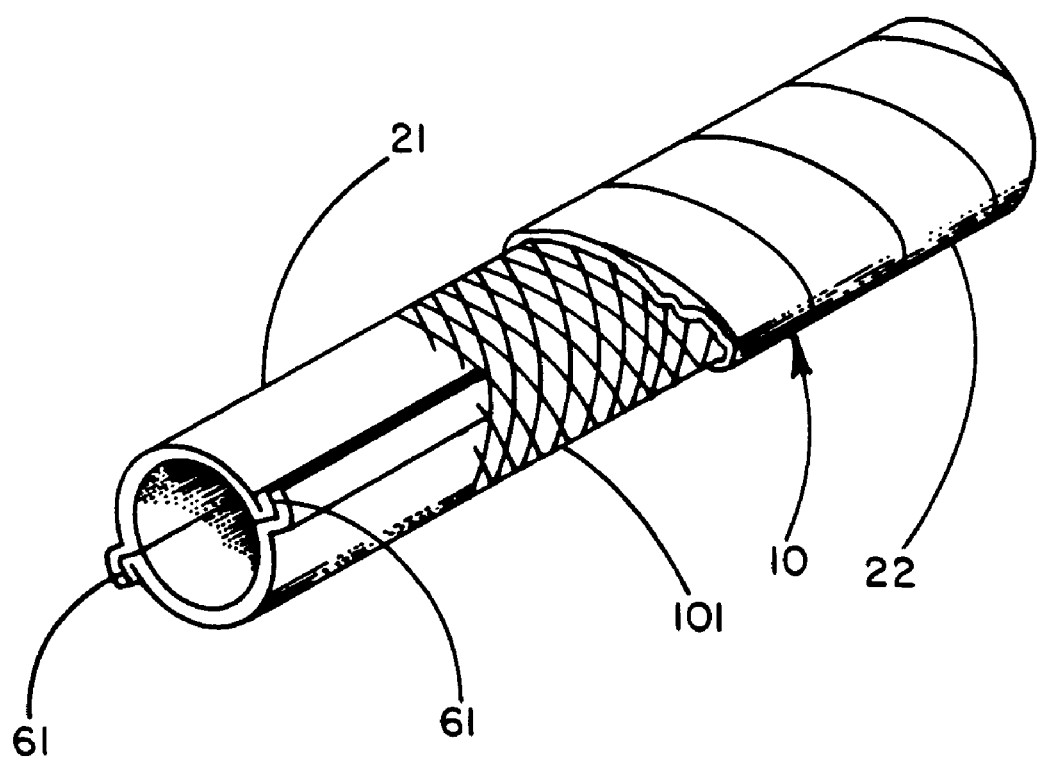
FIG. 10 describes an alternative embodiment of the thin-wall tube incorporating a braided reinforcing layer.

As shown by the cutaway perspective view of FIG. 10, a thin-wall tube 10 incorporating a layer of braided reinforcing material 101 was made by first applying a first layer 21 of film to a 6 mm stainless steel mandrel using the same method and the same 12.5 mm wide film described by Example 4. A roll of the same film used to form the first layer 21 was cut to a width of 6.2 mm. The resulting roll of narrow film was then paid off onto 8 individual small spools. The process of paying the film from the supply roll onto the small spools used enough tension that the narrow film bunched down into a flat thread of about 0.8 mm width and 0.03 mm thickness. This bunching of the porous expanded PTFE film into a thread occurred without any appreciable increase in length. The small spools were then used as supply spools on a Steeger model D-5600 braiding machine to form a braid from the thread on the exterior surface of the film-covered mandrel. The braid density was about 5 picks per cm. After braiding, a helically-wrapped second layer 22 of the same film used for the first layer 21 of this example was applied. The helical wrapping was applied so that each wrap overlapped the edge of the previous wrap by about 2 mm. The braided and film-wrapped mandrel was then placed into an oven set at 383° C. for a period of 15 minutes, removed and allowed to cool. After removal of the mandrel from the thin-wall tube, the wall thickness of this tube was determined to be 0.06 mm. The mechanical integrity of a 12 cm long sample of this tube was challenged by inserting a latex balloon of 6 mm outside diameter into the lumen of the sample and pressurizing the balloon with air at a pressure of 3.5 kg/cm$^2$ for 3 minutes. Inflation to this pressure required about five seconds of time which was not included in the 3 minute test time. This test caused no visible damage to the thin-wall tube.

EXAMPLE 6

A thin-wall tube was made incorporating a helically-oriented metal wire as a reinforcing rib. Discontinuous FEP-coated porous expanded PTFE film was wrapped around a 38 mm diameter, 1.5 meter long tubular stainless steel mandrel. The film used was of the type described previously in Example 3, except that the film was about 140 mm wide. A 1.0 meter length of this film was longitudinally wrapped in a single layer around the mandrel with the longitudinally-oriented film edges slightly overlapping, with the fibrils of the porous expanded PTFE film oriented parallel to the longitudinal axis of the mandrel and with the discontinuously FEP-coated surface of the film facing away from the surface of the mandrel, that is, not in contact with the mandrel surface. Next, a single layer of porous expanded PTFE filter membrane (Part No. 13203NA, Frazier No. 8.3, W. L. Gore & Associates, Inc., Cherry Hill, N.J.) was wrapped over the previous layer of porous expanded PTFE film. Again, the wrap was accomplished with a slight overlap of the longitudinal edges of the filter membrane and with the fibrils of the filter membrane oriented parallel to the longitudinal axis of the mandrel. A 0.15 mm diameter stainless steel wire (304V, Ft. Wayne Metals Research Products Corp., Fort Wayne Ind.) was helically wrapped over the film-covered portion of the mandrel with adjacent windings of the wire spaced about 1.0 cm apart. Finally, a length of 1.9 cm wide film of the same type used against the surface of the mandrel was helically wrapped over the film and wire-covered portion of the mandrel. The discontinuously FEP-coated surface of this film faced inwardly toward the mandrel surface. The helical wrapping was accomplished with adjacent edges of the wrapping spaced about 0.46 cm apart; the fibrils of the porous expanded PTFE were oriented parallel to the length of the helically-wrapped film, that is, the fibrils were helically oriented about the circumference of the mandrel. The mandrel was then placed into an air convection oven set at 350° C. for seven minutes. A thermocouple attached to a bare steel portion of the mandrel surface indicated a temperature of 325° C. at the end of the seven minutes, at which time the mandrel was removed from the oven and allowed to cool to room temperature. The porous expanded PTFE film and wire composite was then removed from the mandrel. This composite had extremely good flexibility and appeared to be mechanically quite strong in spite of only having a wall thickness of 0.05 mm exclusive of the helically-oriented steel wire. Because of the filter membrane layer it was anticipated that this tubular composite would perform as an effective filter device.

It is apparent that the foregoing examples are illustrative only and that the sequence, number and characteristics of the various layers of the thin-wall tube may be changed as desired.

We claim:
1. A medical device comprising permeable, porous expanded polytetrafluoroethylene tube having a microstructure of nodes interconnected by fibrils and provided with a non-porous coating over the porous expanded polytetrafluoroethylene, wherein the tube is non-porous, wherein said tube is an inflatable balloon.

2. A medical device according to claim 1 wherein the non-porous coating comprises fluorinated ethylene propylene.

3. A medical device according to claim 1 wherein the porous expanded polytetrafluoroethylene comprises multiple layers.

4. A medical device according to claim 1 wherein the balloon is an inelastic balloon.

5. A medical device according to claim 1 wherein balloon comprises a portion of a balloon catheter.

6. A medical device according to claim 1 wherein the non-porous coating is a continuous coating.

7. A medical device according to claim 1 wherein the non-porous coating comprises an adhesive.

8. A medical device according to claim 7 wherein the adhesive comprises a thermoplastic adhesive.

9. A medical device according to claim 8 wherein the thermoplastic adhesive is a thermoplastic fluoropolymer.

* * * * *